United States Patent

Griffith et al.

[11] Patent Number: 6,127,420
[45] Date of Patent: Oct. 3, 2000

[54] L-N⁵-(1-IMINO-3-ALKENYL) ORNITHINE AND RELATED COMPOUNDS AND USE THEREOF

[75] Inventors: Owen W. Griffith; Ramesh Babu Boga, both of Milwaukee, Wis.

[73] Assignee: The Medical College of Wisconsin Research Foundation, Inc., Milwaukee, Wis.

[21] Appl. No.: 09/131,194

[22] Filed: Aug. 7, 1998

Related U.S. Application Data

[60] Provisional application No. 60/056,650, Aug. 22, 1997.

[51] Int. Cl.⁷ .................. C07L 251/14; A61K 31/197
[52] U.S. Cl. .............................. 514/564; 562/560
[58] Field of Search ............... 562/560; 514/564

[56] References Cited

U.S. PATENT DOCUMENTS 5,281,627  1/1994  Griffith ...................... 514/565

OTHER PUBLICATIONS

Babu, R. B., et al, J. Biol. Chem., 273, No. 15 8882–8889 (Apr. 10, 1998).
Silverman R. B., J. Med. Chem. 40, 2813–2817 (1997).
Medline Abstract of Samii, S. A., et al, Am. J. Physiol., 267, E124–E134 (1994); Identifier 94324471.
Medline Abstract of Bickel, U., et al, J. Pharm. Expt. Therap. 268(2), 791–796 (1994); Identifier 94157782.
Medline Abstract of Toth, I., J. Drug Targeting 2, 217–239 (1994); Identifier 95111928.
Medline Abstract of Tamai, I., et al, J. Pharmacol. Expt. Therap. 280, 410–415 (1997); Identifier 97149414.
Abstract of Pietrowski, R., et al. Biol. Psych. 39, 332–340 (1996); PMID:8704064; UI:96252654.
Scannell, J. P., et al, The Journal of Antibiotics, vol. XXV, No. 3, 179–184 (Mar. 1972).
Palacios, M., et al, Biochem. Biophys. Res. Commun., 165, No. 2, 802–809 (Dec. 1989).
Rees, D. D., et al, Br. J. Pharmacol., 101, 746–752 (1990).
McCall, T. B., et al, Br. J. Pharmacol., 102, 234–238 (1991).
Moore, W. M., et al, J. Med. Chem., 37, 3886–3888 (1994).

*Primary Examiner*—Robert Gerstl

[57] ABSTRACT

Selective and irreversible inhibitors of neuronal isoform of nitric oxide synthase catalyzed production of nitric oxide are L-ornithine or L-lysine derivatives having the formula

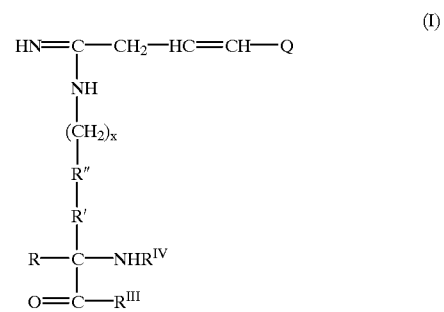

wherein Q is H or $(CH_2)_r CH_3$ where r ranges from 0 to 15, x is 1 or 2, R" is $CH_2$ or $C(H)(CH_2)_y CH_3$ where y ranges from 0 to 5, R' is $CH_2$ or $C(H)(CH_2)_z CH_3$ where z ranges from 0 to 5, R is H or $(CH_2)_s CH_3$ where s ranges from 0 to 5, with none or only one of R, R' and R" providing an alkyl substituent on ornithine or lysine moiety, $R^{III}$ is OH or is an alkoxy group of 1 to 6 carbon atoms or is an amino acid or peptide attached in amide linkage through its free α-amino group, and $R^{IV}$ is —H or an acyl group of 1 to 6 carbon atoms or is an amino acid or peptide attached in amide linkage through its free α-carboxylate group, and mixtures thereof with corresponding D-isomers. A preferred compound is $N^5$-(1-imino-3-butenyl)-L-ornithine. The compounds are useful for treatment of migraine headaches, stroke, pain due to stimulation of nNOS-containing neurons including chronic visceral pain, drug addiction, Parkinson's disease, schizophrenia, and epilepsy.

16 Claims, 3 Drawing Sheets

L-N⁵-(1-IMINO-3-ALKENYL) ORNITHINE AND RELATED COMPOUNDS AND USE THEREOF

CROSS-REFERENCE TO RELATED APPLICATION

This application claims the benefit of U.S. Provisional Application No. 60/056,650, filed Aug. 22, 1997.

The invention was made at least in part with United States Government support under National Institutes of Health grant DK48423. The United States Government has certain rights in the invention.

TECHNICAL FIELD

The invention is directed at certain ornithine and lysine derivatives which are selective, mechanism-based inactivators of neuronal isoform of nitric oxide synthase and selective inhibitors of nitric oxide synthase.

BACKGROUND OF THE INVENTION

Nitric oxide synthase (NOS) catalyzes the oxidation of L-arginine to nitric oxide (NO) and citrulline; NADPH and $O_2$ are cosubstrates. Three major isoforms of NOS have been identified to date. The neuronal (nNOS) and endothelial (eNOS) isoforms are constitutively expressed and are regulated by $Ca^{2+}$/calmodulin, whereas the activity of the inducible isoform (iNOS) is controlled transcriptionally and is not affected by changes in intracellular $Ca^{2+}$. The three isoforms are all comprised of a C-terminal reductase domain that binds NADPH and the cofactors FAD and FMN and an N-terminal oxygenase domain that binds L-arginine and heme and tetrahydrobiopterin cofactors.

Nitric oxide synthase-derived NO is important in many physiological processes including blood pressure homeostasis, neurotransmission and immune function, but overproduction of NO can have pathological consequences. For example, excess NO resulting from overexpression of iNOS in response to endotoxin or inflammatory cytokines is a major contributor to the vascular disregulation seen in septic shock and in patients receiving interleukin-2-based immunotherapy. Inappropriate activation of nNOS is implicated in chronic visceral pain, in migraine headache, and in several neurodegenerative diseases (e.g., Parkinson's disease) and contributes to post-ischemic reperfusion injury in stroke.

Because NO has beneficial effects, there is great interest in NOS inhibitors that preferentially inhibit only the NOS isoform causing the particular pathology being treated. For example, iNOS specific inhibitors are of interest as drugs for the treatment of a variety of inflammatory and autoimmune conditions. Inhibitors that preferentially inhibit nNOS are of interest for the treatment of migraine headaches, mild to moderate pain due to the stimulation of nNOS-containing neurons including chronic visceral pain, stroke, Parkinson's disease, schizophrenia, drug abuse and epilepsy.

It has been shown that the S-alkyl-L-thiocitrullines show modest selectivity (up to 50-fold) for nNOS over eNOS and iNOS, and it has been proposed that these compounds may be of use in treating disorders involving overstimulation of nNOS (e.g., stroke). Improved potency and isoform selectivity would, however, be highly desirable. Moreover, the S-alkyl-L-thiocitrullines are reversible inhibitors of nNOS, so they would have to be administered repetitively in successive doses. An irreversible inhibitor of nNOS would have the advantage of requiring only a few or a single administration(s).

SUMMARY OF THE INVENTION

The invention herein is directed to neuronal isoform selective mechanism-based inactivators and neuronal isoform selective inhibitors, of nitric oxide synthase. These selective inactivators and inhibitors of nitric oxide synthase are L-ornithine or L-lysine derivatives having the formula

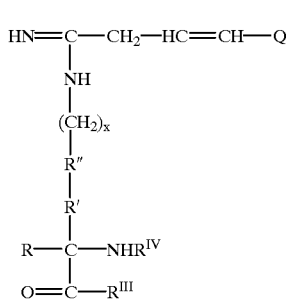

wherein Q is H or $(CH_2)_rCH_3$ where r ranges from 0 to 15, x 1 or 2, R" is $CH_2$ or $C(H)(CH_2)_yCH_3$ where y ranges from 0 to 5, R' is $CH_2$ or $C(H)(CH_2)_zCH_3$ where z ranges from 0 to 5, R is H or $(CH_2)_sCH_3$ where s ranges from 0 to 5, with none or only one of R, R' and R" providing an alkyl substituent on ornithine or lysine moiety, $R^{III}$ is OH or is an alkoxy group of 1 to 6 carbon atoms or is an amino acid or peptide attached in amide linkage through its free α-amino group, and $R^{IV}$ is —H or an acyl group of 1 to 6 carbon atoms or is an amino acid or peptide attached in amide linkage through its free α-carboxylate group, and mixtures thereof with corresponding D-isomers of the L-ornithine or L-lysine derivatives.

The L-isomers are depicted and the invention herein embraces the purified L-isomers and L-isomers in admixture with the corresponding D-isomer, e.g., the corresponding DL-compounds. The corresponding D-isomers are inactive as inactivators of nitric oxide synthase and as inhibitors of nitric oxide production. Thus, the compounds herein are stereospecific.

The unsaturation in the three-position of the alkenyl group rather than unsaturation in a different position of the alkenyl group is necessary for inhibition of nitric oxide production catalyzed by nNOS.

The term "mechanism-based" is used herein to mean irreversible inactivation considered to occur by the route of compound of the genus described above covalently reacting with the nNOS enzyme by binding initially to the arginine binding site whereupon the enzyme attempts to use the compound as a substrate and activates the compound to a species that covalently reacts with heme cofactor and/or nNOS protein and thereby inactivates (irreversibly inhibits) the enzyme.

The term "selective" is used herein to mean that the $K_i$ for the compound divided by the $K_m$ for L-arginine is less for nNOS than for eNOS and iNOS.

For determination of $K_i$ of a compound, activity of NOS is determined by monitoring the conversion of L-[$^{14}$C] arginine to L-[$^{14}$C]citrulline. For determinations of $K_i$ for the compound for nNOS and eNOS, reaction mixtures contain in a final volume of 50 μl, 50 mM Na⁺ Hepes buffer, pH 7.4, 100 μM EDTA, 0.2 mM $CaCl_2$, 10 μg/ml calmodulin, 100 μM dithiothreitol, 50 μM tetrahydrobiopterin, 1.0 μM flavin-adenine dinucleotide, 1.0 μM flavin mononucleotide, 100 μg/ml bovine serum albumin, 500 μM NADPH, L-[$^{14}$C]arginine of varying concentration, compound for which the $K_i$ is being determined of varying concentration, and nNOS or eNOS. Reaction mixtures for iNOS are similar, but $CaCl_2$ and calmodulin are omitted. Reaction is initiated by the addition of the enzyme, and the solutions are maintained at 25° C. for 4 min. Reaction mixtures are quenched by the addition of 200 μl of stop buffer containing 100 mM $Na^+$ Hepes buffer, pH 5.5, and 5 mM ethylene glycol bis (β-aminoethylether)-N,N,N',N"-tetraacetic acid (EGTA). The resulting samples are heated in a boiling water bath for 1 minute and chilled and centrifuged. A portion (225 μl) of the supernatant is applied to small Dowex 50 columns ($Na^+$ form, 1 ml resin), and the product L-[$^{14}$C]citrulline is eluted with 2 ml of water and quantified by liquid scintillation counting.

$K_m$ is the Michaelis-Menton constant for L-arginine determined in the absence of inhibitor by the method set forth in the paragraph directly above this one; it reflects the affinity with which L-arginine binds to enzyme during catalysis where a smaller $K_m$ indicates greater affinity.

A preferred compound embraced by the above-described genus is $N^5$-(1-imino-3-butenyl)-L-ornithine which is sometimes referred to herein as L-VNIO and is sometimes referred to in provisional application No. 60/056,650 as allyl-L-NIO or ALNIO.

Another embodiment of the invention herein is directed to a method for selectively and irreversibly inhibiting neuronal isoform of nitric oxide synthase catalyzed production of nitric oxide in a subject in need of such inhibition, said method comprising administering a neuronal isoform of nitric oxide synthase catalyzed production inhibiting amount of a compound of formula (I) described above to the subject.

The term "subject" is used herein to mean any mammal, including human, where nitric oxide formation from arginine catalyzed by nNOS occurs. The method herein for use on subjects contemplates prophylactic use (prophylaxis) as well as curative use in therapy of an existing condition. The term "prophylaxis" is used herein to mean administration to a subject at risk for a condition to prevent or delay the occurrence of the condition or to ameliorate the symptoms of the condition should it occur compared to where administration is not carried out.

DETAILED DESCRIPTION

Figure 1:
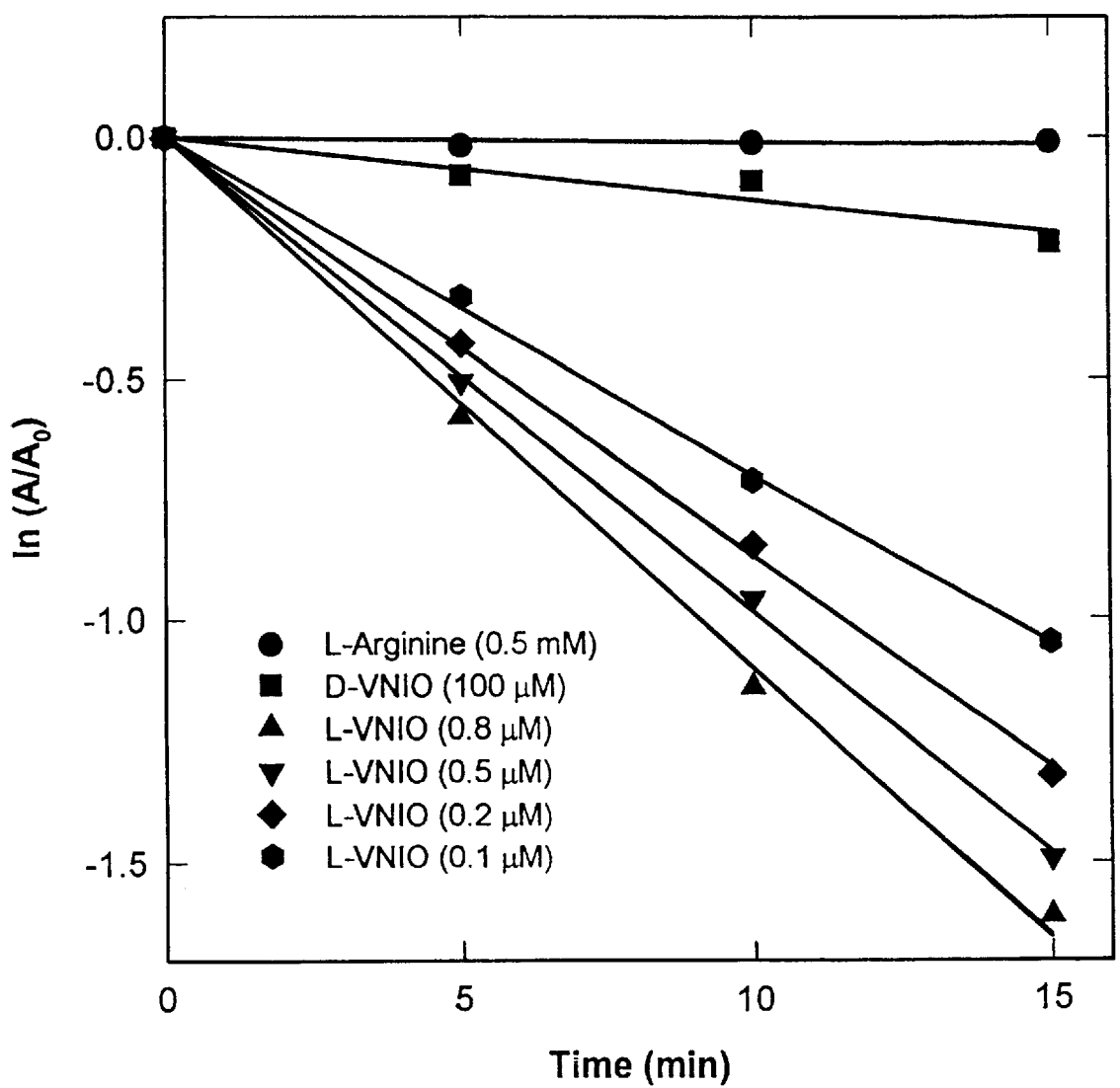
FIG. 1 is a graph showing time- and concentration-dependent inactivation kinetics of L-VNIO with nNOS at 25° C. and shows comparison to the corresponding D-isomer.

We turn now to the compounds herein having the above-described formula where x is 1, R is H, R' is $CH_2$, R" is $CH_2$, $R^{III}$ is OH and $R^{IV}$ is H. These compounds include, for example, $N^5$-(1-imino-3-butenyl)-L-ornithine, $N^5$-(1-imino-3-dodecenyl)-L-ornithine, $N^5$-(1-imino-3-octadecenyl)-L-ornithine, $N^5$-(1-imino-3-pentenyl)-L-ornithine, $N^5$-(1-imino-3-hexenyl)-L-ornithine, $N^5$-(1-imino-3-heptenyl)-L-ornithine, $N^5$-(1-imino-3-isopentenyl)-L-ornithine, and $N^5$-(1-imino-3-isohexenyl)-L-ornithine. These compounds can be prepared by reacting copper acetate with L-ornithine HCl to bind to and block the alpha amino and carboxylate functionalities leaving the side chain amino group as the sole reactive group. The L-ornithine copper salt is reacted with the appropriate alkyl imidate $$QCH=CH-CH_2-\underset{\underset{CH_3}{|}}{\underset{|}{\overset{|}{C}}}-NH_2^+Cl^-$$
$$\phantom{QCH=CH-CH_2-}O$$

where Q is defined as above, in molar proportions ranging from 0.5 to 1.5 L-ornithine copper salt to imidate. The alkyl imidate is prepared by reacting a starting nitrile $$QCH=CH-CH_2-C\equiv N$$

where Q is defined as above, with methanol and HCl. In the reaction of the L-ornithine copper salt with the alkyl imidate the —O—$CH_3$ moiety is removed and the carbon from which it is removed is joined to the side chain nitrogen. Hydrogen sulfide gas is then added to the reaction mixture to remove the copper blocking the alpha amino group and the carboxylate.

We turn now to the compounds herein having the above-described formula where x is 2, R is H, R' is $CH_2$, R" is $CH_2$, $R^{III}$ is OH and $R^{IV}$ is H. These compounds include, for example, $N^6$-(1-imino-3-butenyl)-L-lysine, $N^6$-(1-imino-3-decenyl)-L-lysine, $N^6$-(1-imino-3-tetradecenyl)-L-lysine, $N^6$-(1-imino-3-pentenyl)-L-lysine, $N^6$-(1-imino-3-hexenyl)-L-lysine, $N^6$-(1-imino-3-heptenyl)-L-lysine, $N^6$-(1-imino-3-isopentenyl)-L-lysine, and $N^6$-(1-imino-3-isohexenyl)-L-lysine. These compounds can be prepared in the same way as the corresponding ornithine compounds except that L-lysine is substituted for L-ornithine.

We turn now to the compounds herein having the above-described formula when x is 1, R is $(CH_2)_sCH_3$ where s ranges from 0 to 5, R' is $CH_2$, R" is $CH_2$, $R^{III}$ is OH and $R^{IV}$ is H. These compounds include, for example, α-methyl-$N^5$-(1-imino-3-butenyl)-L-ornithine, α-hexyl-$N^5$-(1-imino-3-butenyl)-L-ornithine, α-pentyl-$N^5$-(1-imino-3-pentenyl)-L-ornithine, α-methyl-$N^5$-(1-imino-3-pentenyl)-L-ornithine and α-ethyl-$N^5$-(1-imino-3-butenyl)-L-ornithine. These compounds can be prepared in the same way as the compounds where x is 0, R is H, R' is $CH_2$, R" is $CH_2$, $R^{III}$ is OH and $R^{IV}$ is H except that α-alkyl-L-ornithine is used in place of L-ornithine. The α-alkyl-L-ornithine can be that present in α-alkyl-DL-ornithine; α-methyl-DL-ornithine is commercially available from Sigma Chemicals, Saint Louis, Mo. The other α-alkyl-DL-ornithines can be prepared from the γ-ketonitrile having the structure $$\underset{\underset{C\equiv N}{|}}{\underset{\underset{(CH_2)_2}{|}}{\underset{\underset{C=O}{|}}{R}}}$$

where R is $(CH_2)_sCH_3$ as defined above, by Strecker amino acid synthesis to the hydantoin followed by reduction of the nitrile group by catalytic hydrogenation and hydrolyzing the reduced product to form amino acid. Alternatively α-alkylornithines can be synthesized by simple extension of the method used for α-methylornithine as described in Denny et al. U.S. Pat. No. 4,061,542. The α-alkyl-DL-ornithine can be used as a reactant to produce α-alkyl-$N^5$-(1-imino-3-alkenyl)-DL-ornithine where the L-isomer is present in admixture and the admixture used or the L-isomer can be purified from the α-alkyl-DL-ornithine (e.g., by chromatography on a chiral support or chromatography using a chiral solvent or by processing comprising forming the α-δ-dichloroacetyl derivative and treating with acylase I, which selectively removes the chloroacetyl group from the α-amino function of the L-enantiomer only), for use as reactant to produce α-alkyl-$N^5$-(1-imino-3-alkenyl)-L-ornithine not in admixture with corresponding D-isomer.

We turn now to the compounds herein having the above-described formula where x is 2, R is $(CH_2)_s CH_3$ where s ranges 0 to 5, R' is $CH_2$, and R" is $CH_2$, $R^{III}$ is OH and $R^{IV}$ is H. These compounds include, for example, α-methyl-$N^6$-(1-imino-3-butenyl)-L-lysine, α-pentyl-$N^6$-(1-imino-3-hexenyl)-L-lysine, α-butyl-$N^6$-(1-imino-3-butenyl)-L-lysine, α-methyl-$N^6$-(1-imino-3-butenyl)-L-lysine and α-ethyl-$N^6$-(1-imino-3-butenyl)-L-lysine. These compounds can be prepared in the same way as the compounds where x is 0, R is H, R' is $CH_2$, R" is $CH_2$, $R^{III}$ is OH and $R^{IV}$ is H except that α-alkyl-L-lysine is used in place of L-ornithine. The α-alkyl-L-lysine can be that present in α-alkyl-DL-lysine. The α-alkyl-DL-lysines are prepared from the δ-ketonitrile having the structure

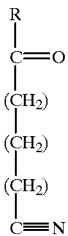

where R is $(CH_2)_s CH_3$ as defined above, by Strecker amino acid synthesis to the hydantoin followed by reduction of the nitrile group by catalytic hydrogenation, and hydrolysis to form amino acid. The α-alkyl-DL-lysine can be used as a reactant to produce α-alkyl-$N^6$-(1-imino-3-alkenyl)-DL-lysine where the L-isomer is present in admixture and the admixture used or the L-isomer can be purified from the α-alkyl-DL-lysine, e.g., by one of the methods described in conjunction with obtaining the L-isomer from α-alkyl-DL-ornithine, for use as a reactant to produce α-alkyl-$N^6$-(1-imino-3-butenyl)-L-lysine, not in admixture with the corresponding D-isomer.

We turn now to the compounds herein having the above described formula where x is 1, R is H, R' is $C(H)(CH_2)_z (CH_3)$ where z ranges from 0 to 5, R" is $CH_2$, $R^{III}$ is OH and $R^{IV}$ is H. These compounds include, for example, β-methyl-$N^5$-(1-imino-3-butenyl)-L-ornithine, β-butyl-$N^5$-(1-imino-3-butenyl)-L-ornithine, β-methyl-$N^5$-(1-imino-3-hexadecenyl)-L-ornithine, β-ethyl-$N^5$-(1-imino-3-butenyl)-L-ornithine, and β-ethyl-$N^5$-(1-imino-3-pentenyl)-L-ornithine. These compounds can be prepared in the same way as the compounds where x is 1, R is H, R' is $CH_2$, R" is $CH_2$, $R^{III}$ is OH, and $R^{IV}$ is H except that β-alkyl-L-ornithine is used in place of L-ornithine. The β-alkyl-L-ornithine can be that present in β-alkyl-DL-ornithine. The β-alkylornithines are synthesized by reaction of ethyl acetamidomalonate with the appropriate β-substituted acrylonitrile in mildly alkaline ethanol at 25°–70° C., followed by catalytic reduction of the nitrile group, followed by acid hydrolysis.

We turn now to the compounds herein having the above-described formula where x is 2, R is H, R' is $C(H)(CH_2)_1 (CH_3)$ where z ranges from 0 to 5, R" is $CH_2$, $R^{III}$ is OH, and $R^{IV}$ is H. These compounds include, for example, β-methyl-$N^6$-(1-imino-3-butenyl)-L-lysine, β-butyl-$N^6$-(-3-heptenyl)-L-lysine, β-methyl-$N^6$-(1-imino-3-octadecenyl)-L-lysine, β-methyl-$N^6$-(1-imino-3-pentenyl)-L-lysine, and β-ethyl-$N^6$-(1-imino-3-butenyl)-L-lysine. These compounds can be prepared in the same way as the compounds where x is 0, R is H, R' is $CH_2$, R" is $CH_2$, $R^{III}$ is OH, and $R^{IV}$ is H except that β-alkyl-L-lysine is used in place of L-ornithine. The β-alkyl-L-lysine can be that present in β-alkyl-DL-lysine. The β-alkyllysines are prepared in the same way as the β-alkylornithines except that γ-bromo-γ-alkylbutyronitrile is used in place of the β-substituted acrylonitrile and 1 molar equivalent of base (e.g., sodium ethoxide) is included in the reaction mixture. Alternative syntheses of β-alkyllysines are well-known in the literature.

We turn now to the compounds herein having the above described formula where x is 1, R is H, R' is $CH_2$, R" is $C(H)(CH_2)_y (CH_3)$ where y ranges from 0 to 5, $R^{III}$ is OH and $R^{IV}$ is H. These compounds include, for example, γ-methyl-$N^5$-(1-imino-3-butenyl)-L-ornithine, γ-methyl-$N^5$-(1-imino-3-eicosenyl)-L-ornithine, γ-ethyl-$N^5$-(1-imino-3-butenyl)-L-ornithine, γ-methyl-$N^5$-(1-imino-3-pentenyl)-L-ornithine, and γ-ethyl-$N^5$-(1-imino-3-pentenyl)-L-ornithine. These compounds can be prepared in the same way as the compounds where x is 0, R is H, R' is $CH_2$, R" is $CH_2$, $R^{III}$ is OH, and $R^{IV}$ is H, except that γ-alkyl-L-ornithine is used in place of L-ornithine. The γ-alkyl-L-ornithine can be that present in γ-alkyl-DL-ornithine. The γ-alkylornithines are synthesized in the same way as the β-alkylornithines except that γ-substituted acrylonitrile is used in place of the β-substituted acrylonitrile.

We turn now to the compounds herein having the above described formula where x is 2, R is H, R' is $CH_2$ and R" is $C(H)(CH_2)_y (CH_3)$ where y ranges from 0 to 5, $R^{III}$ is OH, and $R^{IV}$ is H. These compounds include, for example, γ-methyl-$N^6$-(1-imino-3-butenyl)-L-lysine, γ-methyl-$N^6$-(1-imino-3-octenyl)-L-lysine, γ-propyl-$N^6$-(1-imino-3-butenyl)-L-lysine, γ-methyl-$N^6$-(1-imino-3-pentenyl)-L-lysine, and γ-ethyl-$N^6$-(1-imino-3-butenyl)-L-lysine. These compounds can be prepared in the same way as the compounds where x is 0, R is H, R' is $CH_2$, R" is $CH_2$, $R^{III}$ is OH, $R^{IV}$ is H, except that γ-alkyl-L-lysine is used in place of L-ornithine. The γ-alkyl-L-lysine can be that present in γ-alkyl-DL-lysine. The γ-alkyllysines can be prepared in the same way as described above for the γ-alkylornithines except that β-alkyl-γ-bromobutyronitrile is used in place of the α-substituted acrylonitrile and 1 molar equivalent of base (e.g., sodium ethoxide) is included in the reaction mixture. Alternative syntheses of γ-alkyllysines are well-known in the literature.

We turn now to the cases where $R^{III}$ is an alkoxy of 1 to 6 carbon atoms or is an amino acid or peptide attached in amide linkage through its free α-amino group and/or where $R^{IV}$ is an acyl group of 1 to 6 carbon atoms or is an amino acid or peptide attached in amide linkage through its free α-carboxylate group. In the cases where $R^{III}$ forms an amide group and $R^{IV}$ does not or where $R^{IV}$ forms an amide group but $R^{III}$ does not, the imino-alkenyl ornithine or lysine forms the end group of a peptide. In the cases where $R^{III}$ and $R^{IV}$ both form amide groups, the imino-alkenyl ornithine or lysine forms an interior residue of a peptide. The peptides, esters and N-acylated derivatives serve as pro-drugs of the active agents. In addition, esterification and acylation of the carboxylate and α-amino functions, respectively, increases hydrophobicity and transport into the central nervous system. Incorporation of the imino-alkenyl ornithine or lysine moiety into either end or the interior of a peptide also increases transport into the central nervous system. For example, there are neuropeptides which, when administered intranasally, achieve efficient transport into the central nervous system. Such peptides include dermorphin analogs as described in Samii, S. A., et al., Am. J. Physiol, 267, E124–E131 (1994) and Bickel, U., et al., J. Pharm. Expt. Therap. 268(2), 791–796 (1994), lipid core peptides as described in Toth, I., J. Drug Targeting 2, 217–239 (1994), basic peptide 001-C8 as described in Tamai, I., et al., J. Pharmacol Expt. Therap. 280, 410–415 (1997) and arginine vasopressin as described in Pietrowsky, R., et al., Biol. Psych. 39, 332–340 (1996). The invention includes replacing a lysine or arginine or less preferably, methionine, leucine, isoleucine, or valine residue of such peptide with L-VNIO or analog of L-VNIO whereby the active drug is released when the peptide is degraded within the central nervous system.

Examples of $R^{III}$ being alkoxy group of 1 to 6 carbon atoms and $R^{IV}$ being acyl group of 1 to 6 carbon atoms include L-VNIO ethyl ester and $N^{\alpha}$-acetyl-L-VNIO.

The compounds where $R^{III}$ is alkoxy group of 1 to 6 carbon atoms or an amino acid or peptide attached in amide linkage or where $R^{IV}$ is acyl group of 1 to 6 carbon atoms or an amino acid or peptide attached in amide linkage, may be prepared by the general technique disclosed in Silverman, R. B., et al., J. Med. Chem. 40, 2813–2817 (1997) and by other general techniques which are known for forming esters, amides, and peptides.

We turn now to the uses of the above described compounds. These compounds find use in a method for selectively and irreversibly inhibiting neuronal isoform of nitric oxide synthase catalyzed production of nitric oxide in a subject in need of such inhibition. Said method comprises administering a neuronal isoform of nitric oxide synthase catalyzed production inhibiting amount of a compound of formula I, described above, to the subject.

The subjects include those having or at risk for migraine headaches, pain due the stimulation of nNOS-containing neurons including chronic visceral pain, stroke, Parkinson's disease schizophrenia, drug abuse and epilepsy. The compounds are administered in a therapeutically effective amount. For treatment or prophylaxis of a stroke, a therapeutically effective amount is a neuronal and glial cell protecting amount. In general, the dosage for the compounds herein ranges from 0.01 to 100 mg/kg. A dosage for $N^5$-(1-imino-3-butenyl)-L-ornithine preferably ranges from 1 to 25 mg/kg. A single administration or a small number of administrations is usually appropriate because of the irreversible nature of the inactivation that is caused. The compounds can be administered, for example, by oral and parenteral routes of administration and are considered to cross the blood brain barrier. Alternatively, the compounds can be administered intrathecally in the spinal cord or intraventricularly into the brain. Where the active drug is part of a peptide that is efficiently transported into the brain via intranasal administration, intranasal administration can be a preferred alternative. The compounds may be administered together with a pharmaceutically acceptable carrier. Such carriers include sterile water or physiological saline for parenteral administration. For oral administration, tablets may contain the active ingredient in admixture with conventional pharmaceutically acceptable excipients including inert diluents such as starch, gelatin, lactose and talc.

The above-described compounds can be used in combination with non-steroidal anti-inflammatory drugs for synergistic interaction in the treatment of pain due to the stimulation of nNOS-containing neurons including chronic visceral pain.

The invention is illustrated by the following working examples.

EXAMPLE I

L-Ornithine HCl (1.68 g, 10 mmol) and cupric acetate (0.5 g, 10 mmol) were dissolved in water (20 ml) and stirred for 10 minutes at room temperature. The solution was then filtered to remove minor impurities and cooled to 0° C., and the pH was adjusted to 9.5 by addition of cold 10% NaOH. 3-Butenyl imidate (15 mmol), prepared separately from the corresponding nitrile, methanol and gaseous HCl by the method described in Scannell, J. P., J. Antibiot. 25, 179–184 (1972) was then added, and the mixture was allowed to stir at pH 9.0–9.5 for 1 hour at 0° C. and for 2 hours at room temperature. The pH was then adjusted to 7.4 with cold dilute HCl, and the mixture was stirred at room temperature overnight. Hydrogen sulfide gas was bubbled through the solution, and the resulting copper sulfide precipitate was removed by filtration through charcoal. The filtrate was passed through Chelex to remove any residual $Cu^{2+}$, and the clear solution was evaporated to dryness by rotary evaporation under reduced pressure. The residue was washed with ethyl acetate, and the product was crystallized from ethanol to give pure $N^5$-(1-imino-3-butenyl)-L-ornithine, which may be referred to as L-VNIO—m.p. 162° C. (dec); H NMR($D_2O$) ; δ1.65-2.1 (m, 4H), 3.3 (d, 2H), 3.4 (t, 2H), 3.8 (t, 1H), 5.4 (m, 2H), and 5.95 (m, 1H); $^{13}C$ NMR ($D_2O$): δ25.43, 30.35, 39.37, 44.28, 56.93, 124.16, 131.55, 168.72, and 176.98; FABMS (fast atom bombardment mass spectrometry): m/e 200 (M+H). Examples below establish L-VNIO as the first neuronal isoform selective, mechanism-based amino acid inactivator of NOS.

EXAMPLE II

An equimolar amount of 3-pentenyl imidate is substituted for the 3-butenyl imidate in the preparation of Example I and the product is $N^5$-(1-imino-3-pentenyl)-L-ornithine.

EXAMPLE II

An equimolar amount of L-lysine is substituted for the L-ornithine in the preparation of Example I and the product is $N^6$-(1-imino-3-butenyl)-L-lysine.

EXAMPLE IV

An equimolar amount of α-methyl-DL-ornithine is substituted for the L-ornithine in the preparation of Example I. The α-methyl-DL-ornithine is obtained from Sigma Chemicals, Saint Louis, Mo. The product is α-methyl-$N^5$-(1-imino-3-butenyl)-DL-ornithine.

EXAMPLE V

An equimolar amount of α-methyl-DL-lysine is substituted for the L-ornithine in the preparation of Example I. The product is α-methyl-$N^6$-(1-imino-3-butenyl)-lysine. The synthesis of α-methyl-DL-lysine is described in Griffith U.S. Pat. No. 5,281,627.

EXAMPLE VI

An equimolar amount of R,S-β-methyl-DL-ornithine is substituted for the L-ornithine in Example I. The product is R,S-β-methyl-$N^5$-(1-imino-3-butenyl)-DL-ornithine. The synthesis of R,S-β-methyl-DL-ornithine is described in Griffith U.S. Pat. No. 5,281,627.

EXAMPLE VII

An equimolar amount of R,S-β-methyl-DL-lysine is substituted for the L-lysine in Example I. The product is R,S-β-methyl-N⁶-(1-imino-3-butenyl)-DL-lysine. The synthesis of R,S-β-methyl-DL-lysine is described in Griffith U.S. Pat. No. 5,281,627.

EXAMPLE VIII

An equimolar amount of R,S-γ-methyl-DL-ornithine is substituted for the L-ornithine in the preparation of Example I. The product is R,S-γ-methyl-N⁵-(1-imino-3-butenyl)-DL-ornithine. The synthesis of R,S-γ-methyl-DL-ornithine is described in Griffith U.S. Pat. No. 5,281,627.

EXAMPLE IX

An equimolar amount of R,S-γ-methyl-DL-lysine is substituted for the L-ornithine in the preparation of Example I. The product is R,S-γ-methyl-N⁶-(1-imino-3-butenyl)-DL-lysine. The synthesis of R,S-γ-methyl-DL-lysine is described in Griffith U.S. Pat. No. 5,281,627.

EXAMPLE X

Kinetic dissociation constants $K_i$ were determined by the method described above, for L-VNIO, L-NIO which is N⁵-(1-iminoethyl)-L-ornithine, methyl-L-NIO which is N⁵-(1-iminopropyl)-L-ornithine, and ethyl-L-NIO which is N⁵-(1-iminobutyl)-L-ornithine in respect to nNOS, eNOS and iNOS. The $K_m$ for L-arginine was also determined. The results are set forth in Table I below where the values shown are averages of at least duplicate determinations made under initial rate conditions as described above; duplicate measurements agreed within ±5%. For the determinations, the nNOS was rat nNOS isolated from stably transfected kidney 293 cells (Bredt, D. S., et al., Nature 351, 714–718 (1991) as described in McMillan, K., et al., Proc. Natl. Acad. Sci. USA 89, 11141–11145 (1992); the eNOS was bovine eNOS described in Liu, J., et al., Biochemistry 35, 13277–13281 (1996) and the iNOS was mouse iNOS expressed in *Escherichia coli* obtained from Dr. Bettie S. S. Masters (Department of Biochemistry, University of Texas Health Sciences Center, San Antonio, Tex.).

TABLE I

| Inhibitor or substrate | Kinetic constants and ratios | | | | | |
|---|---|---|---|---|---|---|
| | nNOS | | eNOS | | iNOS | |
| | $K_i$ μM | $K_i/K_m$ | $K_i$ μM | $K_i/K_m$ | $K_i$ μM | $K_i/K_m$ |
| L-VNIO | 0.10 | 0.07 | 12.0 | 3.33 | 60 | 4.80 |
| L-NIO | 1.7 | 1.21 | 3.9 | 1.08 | 3.9 | 0.31 |
| Methyl-L-NIO | 3.0 | 2.14 | 10.0 | 2.78 | 9.5 | 0.76 |
| Ethyl-L-NIO | 5.3 | 3.79 | 18.0 | 5.00 | 12.0 | 0.96 |
| L-Arginine ($K_m$) | 1.4 | | 3.6 | | 12.5 | |

The smaller the $K_i$, the more tightly bound the inhibitor and the better the inhibition. $K_i/K_m<1$ shows the inhibitor is binding more tightly than the substrate, L-arginine. The results show that L-VNIO is a potent inhibitor of nNOS, and a poor inhibitor of eNOS and INOS, and therefore is a selective inhibitor of nNOS. On the other hand, L-NIO, methyl-L-NIO and ethyl-L-NIO, on a $K_i/K_m$ basis, do not show biologically significant selectivity for nNOS over eNOS and show a modest selectivity (3 to 5 fold) for iNOS over nNOS and eNOS.

EXAMPLE XI nNOS obtained as described in Example X was incubated with L-arginine (0.5 mM), with various concentrations of L-VNIO and with a high concentration (100 μM) of N⁵-(1-imino-3-butenyl)-D-ornithine which is denoted D-VNIO at 25° C. The preincubation mixture had a final volume of 0.15 ml and contained 50 mM Na⁺ Hepes buffer, pH 7.4, 0.1 mM EDTA, 50 μm tetrahydrobiopterin, 2.0 mM glutathione, 1.0 μM flavin-adenine dinucleotide (FAD), 1.0 μM flavin mononucleotide (FMN), 1 mg/ml bovine serum albumin, 0.2 mM CaCl₂, 10 μg/ml calmodulin, 1.0 mM NADPH and 0.5 mM of L-arginine or 0.1 μM, 0.2 μM, 0.5 μM or 0.8 μM L-VNIO or 100 μM D-VNIO, superoxide dismutase (100 units) and nNOS (about 40 μg). Residual activity was determined after various time intervals, by adding a 25-μl aliquot of the reaction mixture to a cuvette containing in a final volume of 0.5 mL, 50 mM Hepes buffer, pH 7.4, 0.1 mm EDTA, 50 μM tetrahydrobiopterin, 10 μg/ml calmodulin, 2.0 mM CaCl₂, 0.1 mM glutathione, 1.0 μM FAD, 1 mg/ml bovine serum albumin, 0.5 mM NADPH, and 0.25 mM L-arginine and 5 μM bovine oxyhemoglobin (prepared by reduction with sodium dithionite followed by gel filtration). Nitric oxide-mediated oxidation of oxyhemoglobin was monitored at 401 nm ($\epsilon=0.038$ μM⁻¹); the reference cuvette contained a similar mixture without enzyme. Rates were measured and used to calculate the residual activity. The results are shown in FIG. 1 where for ln A/A₀ in the legend for the vertical axis, A is the residual activity of NOS at the time indicated and A₀ is the activity of NOS at time zero (i.e., initial activity). As shown in FIG. 1, L-VNIO, but not D-VNIO, caused a first-order inactivation of nNOS. The horizontal orientation of a curve shows no loss of activity. A downward slope indicates progressively decreased activity showing that the enzyme is being inactivated.

EXAMPLE XII

Figure 2:
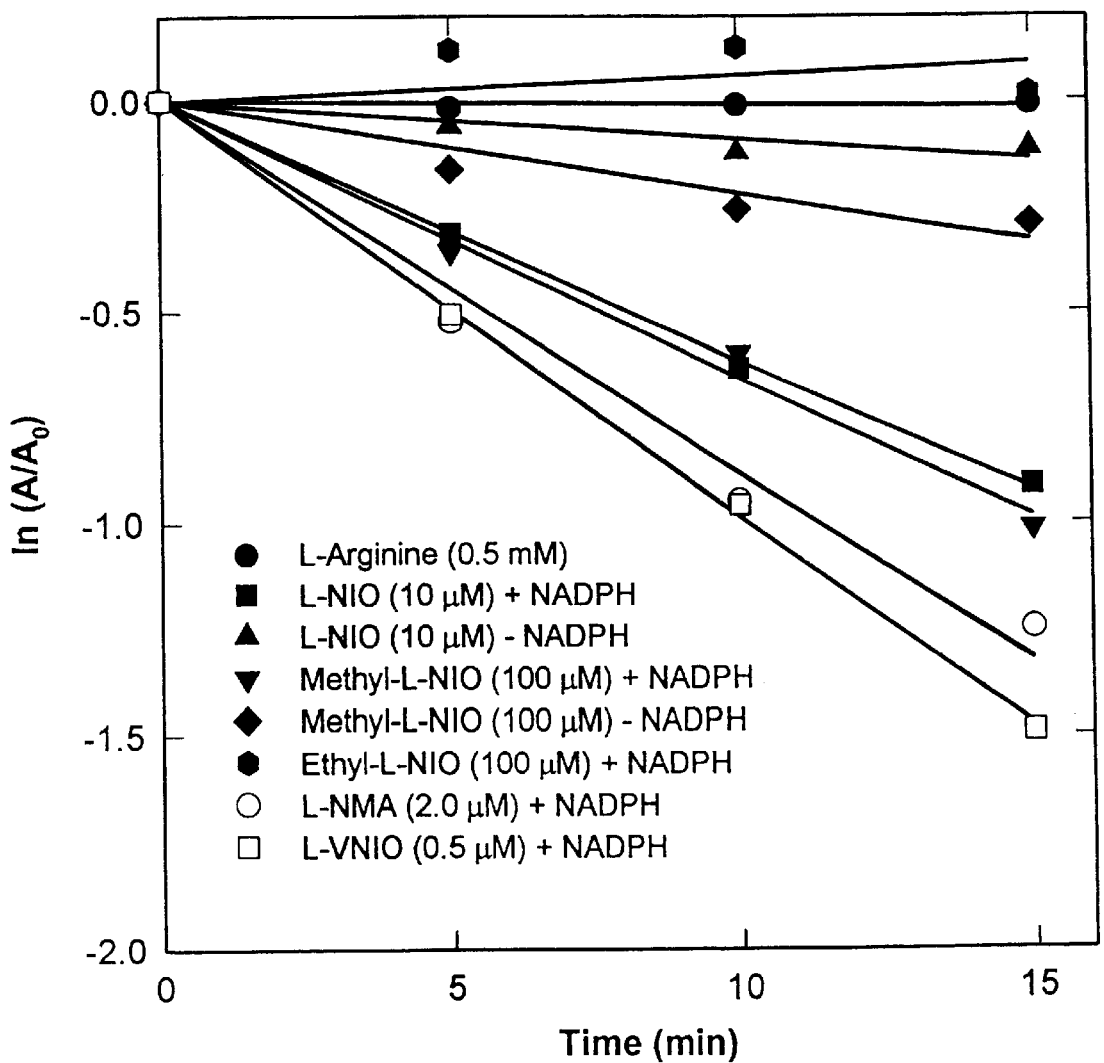
FIG. 2 is a graph showing time-dependent inactivation of L-VNIO with nNOS at 25° C. and shows comparison to L-NIO, methyl-L-NIO, ethyl-L-NIO, and L-NMA.

Comparison was carried out for inactivation of nNOS by L-VNIO, N⁵-(1-iminoethyl)-L-ornithine denoted L-NIO, N⁵-(1-iminopropyl)-L-ornithine denoted methyl-L-NIO, N⁵-(1-iminobutyl)-L-ornithine denoted ethyl-L-NIO and N^ω-methyl-L-arginine denoted L-NMA. Determinations were carried out as described in Example XI. The results are shown in FIG. 2 where in (A/A₀) means the same as in Example XI. As shown in FIG. 2, inactivation by 0.5 μM L-VNIO is comparable with that seen with 2.0 μM L-NMA and greater than that seen with 10 μM L-NIO. Interestingly, the next higher homolog of L-NIO, methyl-L-NIO, is a much weaker inactivator of nNOS requiring a 10-fold higher concentration (100 μM) to duplicate the inactivation seen with L-NIO. Further extension of the iminoalkyl group to form the saturated analog of L-VNIO, i.e., ethyl-L-NIO, results in a compound that does not inactivate nNOS under the conditions examined.

EXAMPLE XIII

Figure 3:
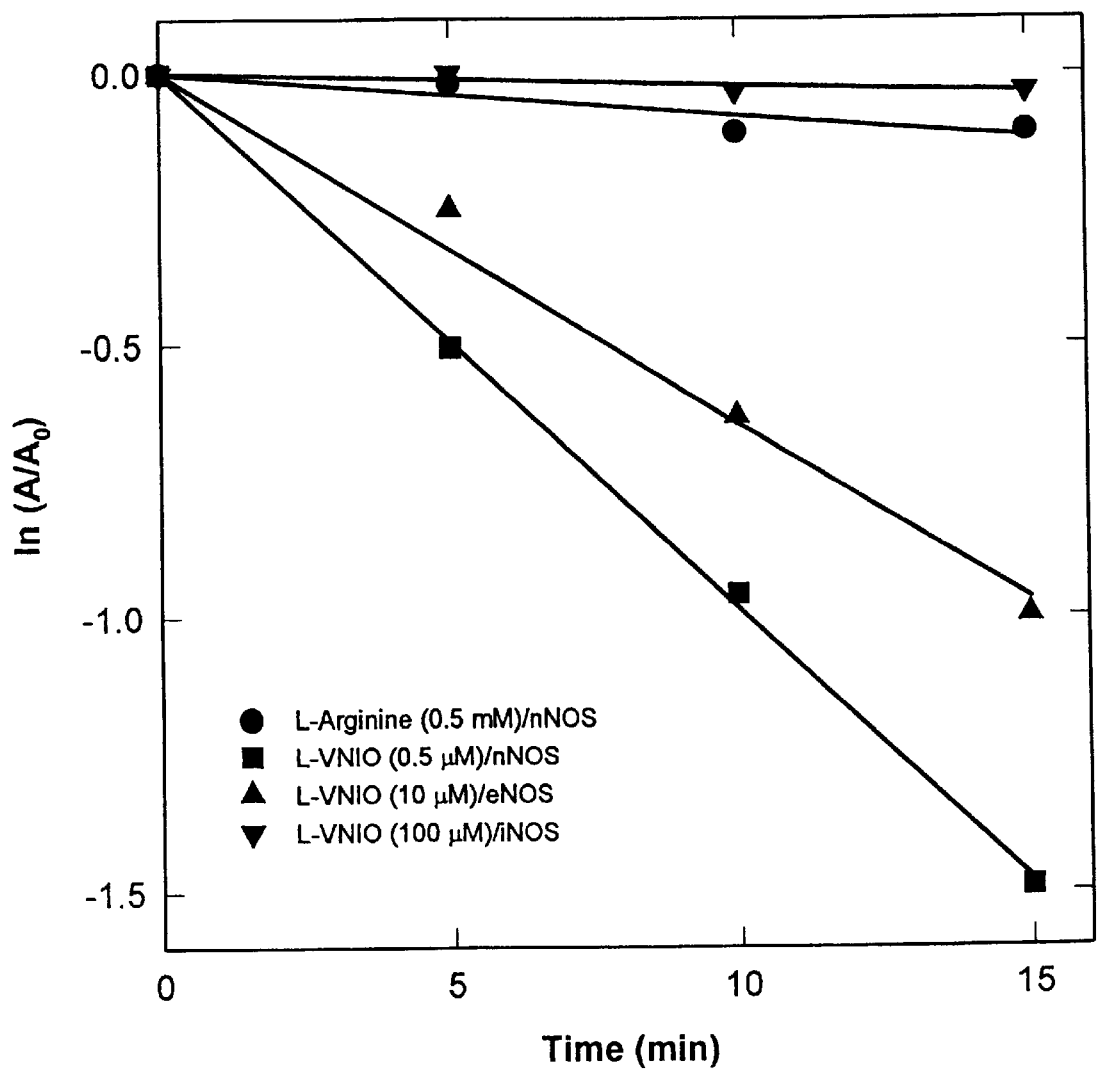
FIG. 3 is a graph showing time-dependent inactivation of L-VNIO with nNOS, eNOS and iNOS at 25° C.

Testing was carried out to compare inactivation by L-VNIO of the nNOS, eNOS and iNOS isoforms. Determinations were carried out as set forth in Example XI except that the reaction mixtures for iNOS omitted CaCl₂ and calmodulin. The isoforms were the same as those described in Example X. The results are shown in FIG. 3. As shown in FIG. 3, L-VNIO is a strong inactivator of nNOS and a relatively weak inactivator of eNOS and does not inactivate iNOS. Even with a 20-fold higher concentration of L-VNIO, the rate of inactivation of eNOS does not match that seen with nNOS (note in FIG. 3, L-VNIO concentration used in respect to nNOS is 0.5 μM and L-VNIO concentration used in respect to eNOS is 10 μM). As shown in FIG. 3, detectable inactivation of iNOS did not occur even with 100 μM L-VNIO

EXAMPLE XIV

Both carotid arteries are ligated in two groups of female Sprague-Dawley CFY rats. After 10 minutes, ligations are released and flow is again allowed.

In the case of one group, L-VNIO (25 mg/kg) is administered by bolus injection through a venous catheter 30 minutes after occlusion of the arteries. In the case of the other group, no therapeutic agent is administered.

Histological analysis of stroke volume 24 hours following artery occlusion shows significant reduction in stroke volume for the group administered L-VNIO compared to the group receiving no treatment.

EXAMPLE XV

A 36 year-old female with a history of migraine headaches is provided with tablets containing 500 mg of L-VNIO. She is instructed to take one tablet at the first sign of migraine headache development and to take a second table 60 minutes later if the headache continues to develop. When a right-sided migraine headache begins, she takes one tablet as instructed, and headache pain begins to decrease within 15 minutes and is absent within 45 minutes. On the following day, a migraine headache develops similarly, but pain is not fully alleviated by the first tablet. The women therefore takes a second table as instructed and headache pain is absent within 30 minutes of taking the second tablet.

Incorporation By Reference

The invention herein is supported by application Ser. No. 60/056,650 which is incorporated herein by reference.

Variations

Many variations of the above will be obvious to those skilled in the art. Thus, the invention is defined by the claims.

What is claimed is:

1. L-ornithine or L-lysine derivatives having the formula

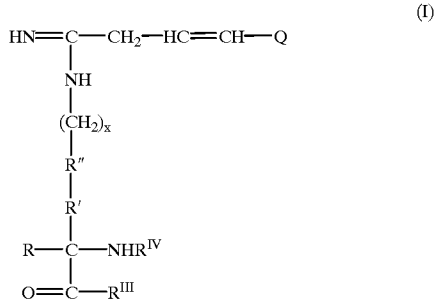

(I)

wherein Q is H or $(CH_2)_r CH_3$ where r ranges from 0 to 15, x is 1 or 2, R" is $CH_2$ or $C(H)(CH_2)_y CH_3$ where y ranges from 0 to 5, R' is $CH_2$ or $C(H)(CH_2)_z CH_3$ where z ranges from 0 to 5, R is H or $(CH_2)_s CH_3$ where s ranges from 0 to 5 with none or only one of R, R' and R" providing an alkyl substituent on ornithine or lysine moiety, $R^{III}$ is OH or is an alkoxy group of 1 to 6 carbon atoms or is an amino acid or peptide attached in amide linkage through its free α-amino group, and $R^{IV}$ is —H or an acyl group of 1 to 6 or is an amino acid or peptide attached in amide linkage through its free α-carboxylate group; and mixtures thereof with corresponding D-isomers of the L-ornithine or L-lysine derivatives.

2. Compound as recited in claim 1 where x is 1.

3. Compound as recited in claim 2 where none of R, R' and R" provides an alkyl substituent on ornithine moiety.

4. Compound as recited in claim 3 which is $N^5$-(1-imino-3-butenyl)-L-ornithine.

5. Compound as recited in claim 2 where R is $(CH_2)_s CH_3$ where s ranges from 0 to 5, R' is $CH_2$ and R" is $CH_2$.

6. Compound as recited in claim 2 where R' is $C(H)(CH_2)_z CH_3$ where z ranges from 0 to 5, R is H and R" is $CH_2$.

7. Compound as recited in claim 2 where R" is $C(H)(CH_2)_y CH_3$ where y ranges from 0 to 5, R is H and R' is $CH_2$.

8. Compound as recited in claim 1 where x is 2.

9. Compound as recited in claim 8 where none of R, R' and R" provides an alkyl substituent on lysine moiety.

10. Compound as recited in claim 9 where R is $(CH_2)_s CH_3$ where s ranges from 0 to 5, R' is $CH_2$ and R" is $CH_2$.

11. Compound as recited in claim 9 where R' is $C(H)(CH_2)_z CH_3$ where z ranges from 0 to 5, R is H and R" is $CH_2$.

12. Compound as recited in claim 9 where R" is $C(H)(CH_2)_y CH_3$ where y ranges from 0 to 5, R is H and R' is $CH_2$.

13. A method for selectively and irreversibly inhibiting neuronal isoform of nitric oxide synthase catalyzed production of nitric oxide in a subject in need of such inhibition, said method comprising administering a neuronal isoform of nitric oxide synthase catalyzed production inhibiting amount of a compound of claim 1 to the subject.

14. The method of claim 13 for prophylaxis or treatment of a subject for a stroke, where the amount of compound of claim 1 is a therapeutically effective amount.

15. The method of claim 14, wherein the therapeutically effective amount is a neuronal and glial cell protecting amount.

16. The method of claim 13 for prophylaxis or treatment of a subject for a migraine headache.

* * * * *